United States Patent [19]

Miller et al.

[11] Patent Number: 4,544,795

[45] Date of Patent: Oct. 1, 1985

[54] ALKYLATION AIDE FOR SULFURIC ACID CATALYZED ALKYLATION UNITS

[75] Inventors: Richard F. Miller, Humble; Michael P. Nicholson, Houston, both of Tex.

[73] Assignee: Atlantic Richfield Company, Los Angeles, Calif.

[21] Appl. No.: 680,032

[22] Filed: Dec. 10, 1984

[51] Int. Cl.$^4$ .............................................. C07C 2/58
[52] U.S. Cl. .................................... 585/721; 585/724; 585/725; 585/730; 585/731
[58] Field of Search ............... 585/721, 724, 725, 730, 585/731

[56] References Cited

U.S. PATENT DOCUMENTS

| | | | |
|---|---|---|---|
| 2,398,905 | 4/1946 | Linn | 585/725 |
| 4,426,545 | 1/1984 | Kramer | 585/721 |
| 4,467,132 | 8/1984 | Go et al. | 585/724 |

*Primary Examiner*—Curtis R. Davis
*Attorney, Agent, or Firm*—Coleman R. Reap

[57] ABSTRACT

The efficiency of acid catalyzed alkylation of alkanes with olefins is improved by conducting the alkylation in the presence of small amounts of a fatty acid having 16 to 40 carbon atoms.

15 Claims, No Drawings

ALKYLATION AIDE FOR SULFURIC ACID CATALYZED ALKYLATION UNITS

FIELD OF THE INVENTION

This invention relates to a process for alkylating hydrocarbons and more particularly to a more improved process of alkylating aliphatic hydrocarbons, particularly branched-chain aliphatic hydrocarbons with olefinic hydrocarbons in the presence of a strong acid.

BACKGROUND

The value of hydrocarbons can often be enhanced by alkylation of lower hydrocarbons to produce higher molecular weight hydrocarbons. For example, isobutanes can be alkylated with isobutene to produce isooctane which is valuable for increasing the octane rating of gasoline. A common commercial method for alkylating a hydrocarbon is to react the hydrocarbon with selected olefins in the presence of a strong acid such as sulfuric acid. Unfortunately, such acid solutions are not readily miscible with organic liquids. Consequently, in alkylation processes catalyzed by strong acids, it has been necessary to use considerable excess acid to effect a commercially feasible degree of alkylation. The unused acid is discarded with the spent acid thereby reducing the efficiency of the process and augmenting the already burdensome waste disposal problem. Improvements which will reduce the amount of acid waste have long been sought.

PRIOR ART

In attempts to improve the efficiency of acid catalyzed alkylations reaction temperatures have been lowered, the mixing efficiency has been increased and the ratio of hydrocarbon to olefin has been varied. None of these techniques has meet with significant success.

Chemical approaches have also been attempted. For example, various chemicals have been added to acid-catalyzed alkylation reaction mixtures to promote more efficient use of the acid catalyst. Thus, U.S. Pat. No. 3,324,196, issued to Kramer et al, discloses the use of an amine or amide containing at least one $C_8$ to $C_{20}$ aliphatic group to promote the acid-catalyzed alkylation of aliphatic and aromatic hydrocarbons. U.S. Pat. No. 2,880,255 discloses the use of mercaptans or combinations of aliphatic amines and mercaptans to promote the alkylation of hydrocarbons.

U.S. Pat. No. 3,778,489 discloses the use of carboxylic acids having 1 to 10 carbon atoms as promoters for the sulfuric acid-catalyzed alkylation of a paraffin with a combination of olefins. U.S. Pat. No. 3,766,293 discloses the use of carboxylic acids having 2 to 10 carbon atoms as promoters for the flurosulfuric acid-catalyzed alkylation of a paraffin with an olefin. U.S. Pat. No. 2,286,184 discloses the use of low molecular weight mono-carboxylic and dicarboxylic acids as modifiers for the sulfuric acid catalyzed alkylation of isoparaffins and olefins.

The present invention is based on the use of chemical additives to promote alkylation reactions. It has been discovered that certain organic acids increase the efficiency of acid-catalyzed alkylation reactions. Accordingly, it is an object of the invention to present an improved alkylation process. It is another object of the invention to present an improved process for alkylating hydrocarbons with acid catalyst. It is another object of the invention to reduce the acid consumption in acid-catalyzed alkylation reactions. These and other objects of the invention are supported in the following description and examples of the invention.

SUMMARY OF THE INVENTION

It has now been discovered that the highly efficient alkylation of aliphatic hydrocarbons by means of strong acid catalysts can be effected by carrying out the alkylation reaction in the presence of at least one fatty acid having about 16–40 or more carbon atoms.

DETAILED DESCRIPTION

Long chain fatty acids usable in the invention include aliphatic acids, other than neo acids, having about 16 to 40 or more carbon atoms. Although fatty acids having more than 40 carbon atoms can be used in the invention, fatty acids having no more than 40 carbon atoms are preferred because they are more readily available and easier to handle. In the preferred embodiment the aliphatic fatty acid has 16 to 36 carbon atoms and in the most preferred embodiment about 16 to 20 carbon atoms per molecule. The fatty acid may be saturated or ethylenically unsaturated and may be linear or branch-chained. The preferred aliphatic fatty acids are the unsaturated fatty acids. As can be appreciated mixtures of two or more fatty acids can be used in the invention. In general, suitable fatty acids are those having the structural formula

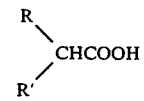

wherein R is hydrogen or a saturated or ethylenically unsaturated, linear or branch-chained hydrocarbon group and R' is a saturated or ethylenically unsaturated linear or branched-chained hydrocarbon group and the average sum of the carbon atoms in R and R' is 14 to 38. Preferably the average sum of the carbon atoms in R and R' is 14 to 34 and most preferably 14 to 18.

Examples of suitable fatty acids include saturated fatty acids, such as palmitic acid, stearic acid, arachidic acid, lignoceric acid, 2-methyl pentadecanoic acid, 2-ethyl palmitic acid, etc. Suitable unsaturated fatty acids include oleic acid, linoleic acid, palmitoleic acid, petroselenic acid, ericic acid, etc. Commercially available hydrolyzed fats and oils and bottoms products contain mixtures of the above fatty acids and these may be conveniently used in the invention. Examples of such fat acids include tall oil fatty acid, palm oil fatty acid, peanut oil fatty acid and cotton seed oil fatty acid. Mixtures of two or more of the above fatty acids and fat acids may also be used in the invention. Preferred acids include stearic acid, oleic acid, linoleic acid and the fat acids such as tall oil fatty acid.

The carboxylic acid alkylation aide may be used in any acid-catalyzed alkylation reaction between hydrocarbons and olefins. Hydrocarbons which are often alkylated include saturated aliphatic and cycloaliphatic hydrocarbons and aromatic hydrocarbons. These alkylation aides are particularly useful in the alkylation of lower branched-chain alkanes, such as isobutane and isopentane with lower olefins to produce octane rating improving additives for gasoline. Lower alkanes which are desirably alkylated include those having 4 to 10 carbon atoms.

Olefins which are used in alkylation reactions include those monoolefins having 3 to 10 carbon atoms. The olefins may be straight- or branched-chain and the olefinic unsaturation may be located anywhere in the structure of the compound.

Particularly useful gasoline additives for increasing the octane rating are the branched octanes such as the compounds or mixture of compounds obtained when isobutane is alkylated with mixed butenes. Branched octanes can also be prepared by the reaction of other alkanes and olefins, for example by the reaction of isopentane and propylene.

Various strong acids are useful for catalyzing the alkylation of aliphatic or aromatic hydrocarbons with an olefin. Sulfuric acid, because of its efficiency and low cost, is the most commonly used acid alkylation catalyst. Other strong acids which can be used include hydrofluoric acid, phosphoric acid and fluorosulfonic acid. Any of the other well known strong acids are also useful for catalyzing alkylation reactions. Strong Lewis acids, such as aluminum bromide, aluminum chloride, antimony pentafluoride, antimony pentachloride, boron trifluoride, etc., can also be used as the acid catalyst in the process of this invention. In general, the alkylation promoters of the invention can be used with any known acid alkylation catalyst.

The alkylation reaction is carried out with all of the reactants in the liquid phase. The temperature of the reaction is that generally used for alkylation reactions. Reaction temperatures can vary from below 0° to as high as or higher than 200° F. The pressure of the reaction is not critical and any pressure which will maintain the reactants substantially in the liquid phase may be employed. Pressures generally range from atmospheric to as high as 100 psi or higher.

The amount of fatty acid promoter added to the reaction mixture usually varies from about 0.0005 to 5.0 percent, based on the total weight of catalyzing acid present in the reaction mixture. Amounts less than 0.0005 weight percent generally produce insignificant results and amounts greater than about 5.0 weight percent are generally unnecessary, although such higher concentrations can be used, if desired. The preferred fatty acid lower concentration is about 0.001 percent and the most preferred minimum level is about 0.0025 percent, based on the total weight of acid catalyst in the reaction mixture. The preferred upper limit of the fatty acid concentration is about 1.0 percent and the most preferred upper limit is about 0.5 percent, based on the total weight of acid catalyst in the reaction mixture. The optimum amount of fatty acid will, of course, vary depending upon the particular fatty acids employed, the particular strong acid catalyst used and the particular hydrocarbons and olefins being reacted.

The alkylation promoters of the invention may be used with other additives, if desired. For example, other alkylation promoters may be used in combination with the promoters of the invention or surfactants or other agents may be added to the reaction mixture.

In a typical application of the invention the hydrocarbon to be alkylated such as a lower branched-chain alkane and an olefin are introduced into a suitable alkylation reaction vessel at a controlled temperature, usually in the range of about 40° to 60° F., and at a pressure sufficiently high to maintain the reactants in the liquid state. The ratio of alkylatable hydrocarbon to olefin alkylating agent is preferably maintained at a high ratio, e.g. about 10:1, to minimize the amount of alkyl sulfate formed by the reaction of olefin with sulfuric acid. An acid alkylation catalyst, such as sulfuric acid, and the fatty acid alkylation promoter are introduced into the reactor, preferably on a continuous basis. At the end of the desired reaction period the finished product is removed from the reaction vessel and separated from the spent acid. The reaction may be carried out on either a batch or continuous basis.

The invention is further illustrated in the following examples. Unless indicated otherwise, parts and percentages are on a weight basis.

EXAMPLE

The efficiency of an alkylation reaction is dependent upon the contact time between the alkylation catalyst and the hydrocarbon being alkylated; the longer the contact time, the more efficient is the alkylation reaction. The alkylation aide increases the catalyst-hydrocarbon contact time. This demonstrates the effectiveness of the alkylation aides of the invention. The test procedure is as follows: Fifty ml of 98% $H_2SO_4$ and 50 ml of iso-octane are introduced into a 100 ml graduate cylinder having a ground glass stopper. In the control run no alkylation additive is used and in the comparative run and the run illustrating the invention 500 ppm of alkylation aide is added to the test mixture. The stoppered cylinder is mechanically shaken for 60 seconds after additive introduction and the time required for the entrained $H_2SO_4$ to separate from the hydrocarbon layer and the time required for the entrained hydrocarbon to separate from the $H_2SO_4$ layer are measured. The results are tabulated in the table.

TABLE

| Run | Additive | Conc. (ppm) | Separation Time (sec.) Hydrocarbon | $H_2SO_4$ |
|---|---|---|---|---|
| 1 | None (Control) | — | 2.38 | 7.12 |
| 2 | Lauric Acid ($C_{12}$) | 500 | 24.02 | 48.94 |
| 3 | Tall oil fatty acid[1] | 500 | 39.48 | 69.20 |

[1]Sold by Westvaco Chemical Company under the trademark L-5.

As illustrated in the example, use of the alkylation aide of the invention (Run 2) results in a significantly greater contact time in both the hydrocarbon and $H_2SO_4$ phases than when no alkylation aide is used.

Although the invention is described with particular reference to specific examples it is understood that the invention includes variations. For example, other hydrocarbons, such as aromatic compounds, may be alkylated or other olefins or acids may be used. The scope of the invention is limited only by the breadth of the appended claims.

We claim:

1. In an alkylation process comprising contacting an alkylatable hydrocarbon with an olefinic alkylating agent at alkylation conditions in the presence of an acid catalyst and an alkylation promoter, the improvement comprising using as the promoter a fatty acid having the structure

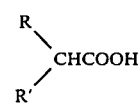

wherein R is hydrogen or a saturated or ethylenically unsaturated hydrocarbon radical and R' is a saturated or ethylenically unsaturated hydrocarbon radical and the average sum of carbon atoms in R and R' is 14 to 38.

2. The improved process of claim 1 wherein the average total sum of carbon atoms in R and R' is 14 to 34.

3. The improved process of claim 1 wherein said alkylatable hydrocarbon is an alkane and said olefinic alkylating agent is a monoolefin.

4. The improved process of claim 3 wherein said alkane has 4 to 10 carbon atoms and said monoolefin has 3 to 10 carbon atoms.

5. The improved process of claim 4 wherein said alkane is branch-chained.

6. The improved process of any one of claims 3 to 5 wherein the concentration of alkylation promoter present in the reaction zone is about 0.0005 to 5.0 percent, based on the total weight of acid catalyst present in the reaction zone.

7. The improved process of any one of claims 3 to 5 wherein the concentration of alkylation promoter present in the reaction zone is about 0.001 to 1.0 percent, based on the total weight of acid catalyst present in the reaction zone.

8. The improved process of claim 6 wherein the average total sum of carbon atoms in R and R' is 14 to 18.

9. The improved process of claim 7 wherein the average total sum of carbon atoms in R and R' is 14 to 18.

10. In an alkylation process comprising contacting a saturated aliphatic hydrocarbon having 4 to 10 carbon atoms with at least one olefinic alkylating agent having 3 to 10 carbon atoms at alkylation conditions in the presence of a strong acid catalyst selected from sulfuric acid, phosphoric acid, hydrofluoric acid, fluorosulfonic acid and mixtures of these and an alkylation promoter, the improvement comprising using as the alkylation promoter about 0.001 to 1.0 percent, based on the total weight of strong acid catalyst of a component comprised of at least one carboxylic acid having the structure

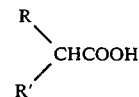

wherein R is hydrogen or a saturated or ethylenically unsaturated hydrocarbon group and R' is a saturated or ethylenically unsaturated hydrocarbon group and the average total sum of carbon atoms in R and R' is 14 to 34.

11. The improved process of claim 10 wherein the average total sum of carbon atoms in R and R' is 14 to 22.

12. The improved process of claim 10 wherein said fatty acid is an unsaturated fatty acid.

13. The improved process of claim 1 wherein said fatty acid is selected from oleic acid, linoleic acid, tall oil fatty acid, palm oil fatty acid, peanut oil fatty acid, cotton oil fatty acid and mixtures of these.

14. The improved process of any one of claims 10 to 12 wherein the saturated aliphatic hydrocarbon is branch-chained.

15. The improved process of claim 14 wherein the alkylation promoter is present in an amount of about 0.0025 to 0.5 percent, based on the total weight of strong acid catalyst present in the reaction zone.

* * * * *